United States Patent
Wrege et al.

(10) Patent No.: US 12,146,998 B2
(45) Date of Patent: Nov. 19, 2024

(54) POSITIONING OF SENSOR UNITS USING A POSITIONING SUBSTRATE

(71) Applicant: Siemens Healthcare GmbH, Erlangen (DE)

(72) Inventors: Jan Wrege, Erlangen (DE); Miguel Labayen de Inza, Forchheim (DE); Robert John Ellwood, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/235,657

(22) Filed: Aug. 18, 2023

(65) Prior Publication Data
US 2024/0061133 A1 Feb. 22, 2024

(30) Foreign Application Priority Data

Aug. 18, 2022 (DE) ...................... 10 2022 208 591.4

(51) Int. Cl.
*G01T 1/24* (2006.01)
*G01T 7/00* (2006.01)

(52) U.S. Cl.
CPC ................ *G01T 1/243* (2013.01); *G01T 7/00* (2013.01)

(58) Field of Classification Search
None
See application file for complete search history.

(56) References Cited

U.S. PATENT DOCUMENTS

| | | | | |
|---|---|---|---|---|
| 10,823,863 | B2 * | 11/2020 | Ergler | ................... G01T 1/244 |
| 2002/0113969 | A1 * | 8/2002 | Case | ................... G02B 6/2553 356/401 |
| 2005/0109946 | A1 | 5/2005 | Von Der Haar | |
| 2008/0165921 | A1 | 7/2008 | Tkaczyk | |
| 2012/0148015 | A1 | 6/2012 | Simon | |
| 2016/0015339 | A1 | 1/2016 | Danzer et al. | |

(Continued)

FOREIGN PATENT DOCUMENTS

| | | |
|---|---|---|
| CN | 101214154 A | 7/2008 |
| CN | 102597807 A | 7/2012 |

(Continued)

OTHER PUBLICATIONS

Decision to Grant for German Application No. 10 2022 208 591.4 decision dated Jun. 13, 2023, with English translation.

(Continued)

*Primary Examiner* — Edwin C Gunberg
(74) *Attorney, Agent, or Firm* — Lempia Summerfield Katz LLC (57) ABSTRACT

A method for positioning sensor units in a detector module for a CT device includes arranging a connecting layer on a positioning substrate. Sensor units and readout units, forming sensor readout arrangements, are positioned relative to the positioning substrate. The sensor units are temporarily connected to the positioning substrate at a fixed position by the connecting layer. Electronics boards are positioned, and conductive connections are produced between the electronics boards and contacts of the readout units, such that sensor boards are obtained. The sensor units are then positioned by the positioning substrate relative to a module carrier and are attached to the module carrier, such that a detector module is obtained.

15 Claims, 3 Drawing Sheets

(56) References Cited

U.S. PATENT DOCUMENTS

2016/0116610 A1    4/2016  Labayen De Inza et al.
2019/0227182 A1    7/2019  Ergler et al.
2021/0011181 A1    1/2021  Hosemann

FOREIGN PATENT DOCUMENTS

| | | |
|---|---|---|
| CN | 211826539 U | 10/2020 |
| CN | 112198543 A | 1/2021 |
| DE | 10354497 A1 | 6/2005 |
| DE | 102014221829 A1 | 4/2016 |
| DE | 102018200845 A1 | 7/2019 |
| DE | 102018216129 A1 | 3/2020 |
| DE | 102014213734 B4 | 1/2021 |

OTHER PUBLICATIONS

German Office Action for German Application No. 10 2022 208 591.4 mailed Mar. 15, 2023, with English translation.

\* cited by examiner

POSITIONING OF SENSOR UNITS USING A POSITIONING SUBSTRATE

This application claims the benefit of German Patent Application No. DE 10 2022 208 591.4, filed on Aug. 18, 2022, which is hereby incorporated by reference in its entirety.

BACKGROUND

The present embodiments relate to positioning sensor units in a detector module for a computed tomography (CT) device using a positioning substrate.

Imaging using X-ray and CT devices is subject to a continuous improvement process. Accordingly, the listing of the devices is always improving, which is also accompanied by ever greater demands on manufacturing precision.

For example, in the case of counting CT detectors, the manufacturing process that is stated below is known from practice. Initially, hybrids that include both a sensor unit or the actual detection material, as well as a readout unit (e.g., an ASIC) are produced. The sensor unit in this case may be conductively connected to the readout unit using a reflow soldering method, where previously, the solder has been introduced as a ball grid array (BGA) between the two units. The readout units of the hybrids that are produced in this manner are attached in a further reflow soldering method act with the introduction of a further ball grid array as solder onto a substrate, and are conductively connected to this substrate. It is possible, using the substrate, for example, to redistribute the electrical connections. Alternatively or in addition thereto, it is possible to arrange on the substrate further electronic components for processing and relaying sensor data. The arrangement of substrate and a number of hybrids may be referred to as a sensor board.

In the case of the above-described manufacturing process, the manufacturing precision of the individual components is important, as is the accuracy of the self-orientation (e.g., floating) of the components during the soldering process.

The requirements of the production tolerances in this case are, however, particularly high. The reason for this is that even small deviations in the subpixel range both in directions within the detection plane (e.g., in the spacings of the sensor units from one another), as well as perpendicular thereto (e.g., (height) stages between the individual sensor units), disadvantageously influence the imaging.

SUMMARY AND DESCRIPTION

The scope of the present invention is defined solely by the appended claims and is not affected to any degree by the statements within this summary.

The present embodiments may obviate one or more of the drawbacks or limitations in the related art. For example, imaging using detector modules for CT devices, production of detector modules for CT devices, or a combination thereof is improved.

The method that is mentioned in the introduction for positioning sensor units in a detector module for a CT device includes at least the following acts. In a first act, a connecting layer is arranged on a positioning substrate. In a further act, a number of sensor units (e.g., a number of readout units) is positioned relative to the positioning substrate, forming sensor readout arrangements. The sensor readout arrangements in this case therefore respectively include a sensor unit and a number of readout units having contacts. In this case, the sensor units are temporarily connected to the positioning substrate at a fixed position by the connecting layer. In one embodiment, a number of electronics boards are positioned in a further act (e.g., relative to the positioning substrate). Further, in this case, a plurality of conductive connections may be produced between the electronics boards and the contacts of the readout units. As a consequence, a number of sensor boards may be obtained. Further, the sensor units and also, for example, the sensor boards are positioned by the positioning substrate relative to a module carrier and are attached to the module carrier. A detector module is obtained as a result.

The positioning substrate is a flat, particularly level substrate that, consequently, has particularly small deviations in its surface in the direction perpendicular to the substrate surface or substrate plane. It is possible, for example, for the positioning substrate to be made from silicon, steel, glass, or another suitable material having similar advantageous surface characteristics. The positioning substrate is used auxiliary for positioning the sensor units relative to the module carrier.

The sensor units typically include a semiconductor material such as, for example, CdTe, CdZnTe, CdZnTeSe, CdTeSe, CdMnTe, InP, TlBr2, HgI2. The sensor units are consequently embodied, for example, as direct-converting sensor units. In other words, the sensor units convert incident photons of suitable wavelength into electrical signals when voltage is applied.

For the duration of the manufacturing process, the connecting layer provides a temporary connection that is at a fixed position in relation to the positioning substrate, between sensor units and the positioning substrate. The connecting layer may be configured, for example, as an adhesive film, coating, tape, or the like. In this case, the connecting layer may include, for example, a suitable polymer. Further characteristics of the connecting layer are stated in further detail below.

"Temporary" in this case provides that the connection may be detached in a further act of the manufacturing process without damaging or destroying the sensor units and the positioning substrate. As a consequence, it is provided that the sensor units may be used regularly in the detector. It is also possible to re-use the positioning substrate for further manufacturing processes. For a new manufacturing process, where necessary, it is possible, however, to apply a new connecting layer to the positioning substrate.

"At a fixed position" in this case provides that the sensor units have neither translational nor rotational degrees of freedom relative to the positioning substrate. The temporary connection between the positioning substrate and the sensor units is in other words rigid.

The term "number" provides that the corresponding feature is included at least once; the corresponding feature may, however, also be included numerous times. Accordingly, the term "plurality" provides that the corresponding feature in each case is included more than once.

Sensor readout arrangements have a sensor unit and a number of readout units. In other words, the sensor readout arrangement includes a sensor unit and one or multiple readout units that read out, and where necessary, evaluate the electrical signals that are generated by incident photons in the sensor material. The sensor readout arrangement in this case is configured, for example, to acquire and, for example, count the electrical signals of even individual incident photons. For this purpose, electrically conductive contacts are formed pixel by pixel between the readout units and the respective sensor unit, which may simultaneously cause a mechanically rigid connection. These contacts may be manufactured in a reflow soldering method, for example, as described in the introduction using solder that is introduced in a ball grid array between the two components. Alternatively, the contacts may also be manufactured, for example, by a pixel by pixel and conductive adhesive. The readout unit may be configured, for example, as an integrated circuit (e.g., as an ASIC). Altogether, the readout unit is, for example, a photon counting sensor readout arrangement.

Also, in order to manufacture the contacts between the electronics board and the readout unit, for example, one of the above-described electrically conductive and, for example, mechanically rigid connecting methods is used. The electronics board is used for the further processing and relaying of the measurement data that is acquired by the sensor unit or the sensor readout arrangement. The electronics board may be configured, for example, as a typical board having corresponding conductor paths and further electronic components. The combination or the mechanical and electronic integration of the electronics board with a number of sensor readout arrangements is referred to as a sensor board.

The module carrier is used as a stabilizing bracket that is to be mounted in the detector in a positionally precise manner. The module carrier is manufactured, for example, from cast aluminum or the like. In order to connect to the detector, the module carrier has precise mechanical connecting elements or the like. The sensor board is attached to the module carrier or is joined together with this module carrier. This may take place, for example, using mechanical connections using a suitable adhesive method or the like. The joined together combination of the module carrier and sensor board is referred to as a detector module. A sensor board is in other words mechanically rigidly connected to the other components of the detector by the module carrier.

The detector module is used in the CT device. The CT device may fundamentally be any arbitrary CT device that is customary in the field. For example, the CT device, however, includes a direct-converting photon-counting detector as already described above. Multiple detector modules are usually installed in a cylinder segment of the CT device, which lies essentially diametrically opposite an X-ray source. The positioning of the detector modules during the installation takes place in this case in general using mechanical positioning that is customary in the field.

In contrast to known manufacturing methods, the positioning precision of the sensor units in relation to the module carrier in accordance with the present embodiments no longer depends upon the positioning accuracies of further layers on the sensor units, such as, for example, the readout units, electronics boards where applicable interposer layers (e.g., rewiring layers), or the like. On the contrary, the positioning precision of the individual sensor units is only still dependent upon the positioning precision relative to the positioning substrate and the positioning precision of the positioning substrate relative to the module carrier.

Even if the further intermediate layers (e.g., the readout units and the electronics boards) may also be positioned in relation to the positioning substrate, inaccuracies in these optional method acts do not affect the precision of the positioning of the sensor units in relation to the module carrier. This provides that inaccuracies that may occur during the "floating" of the components in the case of the individual reflow solder process acts do not have an effect on the positioning precision of the sensor units in relation to the module carrier.

Accordingly, the detector module that is mentioned in the introduction for a CT device may be obtained or may be manufactured by the above-described method in accordance with the present embodiments for positioning sensor units in the detector module.

As mentioned above, a positioning substrate is used so as to position sensor units relative to a module carrier of a detector module of a CT device. In this case, a number of sensor units are positioned relative to the positioning substrate and are temporarily connected to the positioning substrate at a fixed position by a connecting layer. The sensor units are then positioned by the positioning substrate relative to the module carrier and are attached to the module carrier in order to obtain the detector module.

Further, embodiments and developments of the present embodiments are provided in the dependent claims and also the subsequent description, where the claims of a claim category may also be developed in a similar manner to the claims and description parts with regard to another claim category. Further, individual features of different embodiments or variants may be combined to new embodiments or variants.

The deviations or height differences in the surface of the positioning substrate may be smaller than 15 µm, smaller than 10 µm, or less than 5 µm, for example.

In accordance with the present embodiments, the positioning substrate may have optical markers, and the positioning of the number of sensor units and, where necessary, the number of evaluating units or the number of sensor readout arrangements takes place in an image processing-controlled manner. Alternatively or in addition thereto, the positioning substrate may have optical markers, and the positioning of the number of sensor boards relative to the module carrier takes place in an image processing-controlled manner. In one embodiment, the optical markers may be used for the sensor units or the evaluating units or the sensor readout arrangements and/or the sensor boards to be positioned precisely with respect to the positioning substrate or with respect to the module carrier. For this purpose, for example, a camera is used, and the positioning is performed in a control loop (e.g., feedback loop) taking into consideration the acquired image. The positioning precision using the image processing controller in this case in the direction parallel to the surface of the positioning substrate may be more precise than 15 µm, more precise than 10 µm, or more precise than 5 µm. The electronics boards may be positioned using the optical markers relative to the positioning substrate.

The positioning substrate may have first mechanical positioning elements for positioning second mechanical positioning elements of the module carrier. The positioning elements are configured, for example, as defined shaping features. This provides that the positioning elements cooperate, for example, directly or via additional elements such as, for example, a dowel pin, in a positive-fit manner, with the result that the positioning substrate may be positioned with a high degree of precision in relation to the module carrier. In one embodiment, the first mechanical positioning elements may be configured as holes in the positioning substrate.

The second positioning elements may also be configured as holes. The positioning elements are, however, further configured to fit as connecting means (e.g., connectors) to a corresponding module bracket of the detector. The positioning elements may, for example, be configured as a thread that is screwed to the detector or the like.

For example, the holes of the first positioning elements and the second positioning elements have the same clear inner diameter. The first positioning elements and the second positioning elements may be oriented with respect to one another, for example, for positioning using a dowel pin or positioning pin. The dowel pin may fit in this case with particularly tight tolerances into the respective holes. Alternatively, the dowel pin may, for example, also have a conical section for a self-centering of the holes with respect to one another. Overall, consequently, using the method in accordance with the present embodiments, a sensor is positioned in relation to the module carrier with a positioning precision of essentially 20 μm.

In a first variant, the positioning of the number of sensor units and the number of readout units includes at least the following part acts: positioning relative to the positioning substrate and temporarily connecting at least one sensor unit at a fixed position on the positioning substrate using the connecting layer; positioning relative to the positioning substrate and conductively connecting in each case at least one readout unit on the sensor units, which are respectively connected to the positioning substrate, in order to obtain a number of sensor readout arrangements.

In other words, in this first variant, initially, therefore, the sensor units are positioned separately on the positioning substrate, and only later are the readout units positioned and connected to the sensor units. In this variant, the positioning elements of the positioning substrate are therefore, where necessary, used for the exact positioning of the readout units relative to the positioning substrate.

In a second variant, the positioning of the number of sensor units and the number of readout units includes at least the following part acts: positioning relative to one another and conductively connecting at least one readout unit on a respective sensor unit in order to obtain a number of sensor readout arrangements; positioning the number (e.g., a plurality) of sensor readout arrangements relative to the positioning substrate, where the sensor units of the number of sensor readout arrangements are temporarily connected to the positioning substrate at a fixed position using the connecting layer.

In other words, in this first variant, initially, therefore, the sensor units are positioned relative to the readout units and are connected to the readout units. Later, the combined sensor-readout arrangements and, for example, their sensors are then positioned relative to the positioning substrate. This variant has the advantage that the sensor readout arrangements may already be prefabricated. In this case, however, the positioning precision of the sensor units with respect to the positioning substrate is not reduced with respect to the other variant.

In one embodiment, the electronics boards are configured as flexible electronics boards, rigid flexible electronics boards, fixed-flexible-fixed electronics boards, or fixed electronics boards. These boards are particularly suitable for use in a CT device or its detector. The boards are selected when designing the detector depending on the requirement for their stability, flexibility, thickness, or similar mechanical characteristics, or for characteristics that are advantageous for the electrical relay.

The positioning substrate may be made from silicon, steel or, for example, glass. All of these materials, when suitably prepared, only have small deviations or height differences in their surface, as already indicated above. The use of glass offers the advantage that the optical positioning elements for the image processing-controlled positioning may also be acquired through the substrate by a camera or the like. This provides that the positioning substrate may be transparent for optical radiation. As a consequence, the image processing-controlled positioning is additionally facilitated.

The connecting layer may have a thermal, an optical, a chemical, and/or a mechanical detaching characteristic, or a corresponding detaching mechanism.

In the case of a thermal detaching characteristic, the connecting layer is cooled below a defined temperature or is heated above a defined temperature in order to render possible or to facilitate the detachment of the sensor units. For this purpose, for example, essentially only the positioning substrate and the connecting layer are heated or cooled and not the further components that are still connected thereto. In this case, the defined temperature is selected so that on one side (e.g., the solder points), the melting point of the solder is not reached, and simultaneously, none of the components are damaged. The, for example, local temperature effect, however, causes the connecting layer to become, for example, brittle, liquid, or the like. In any case, the bond of the sensor units to the connecting layer is weakened on account of the temperature effect.

In the case of an optical detaching characteristic, the connecting layer is irradiated with light of a defined wavelength in order to weaken the bond of the sensor units to the connecting layer. In this case, the radiation is, for example, in the ultraviolet range (e.g., UV radiation) or the like.

In the case of a chemical detaching characteristic, the connecting layer is immersed, for example, in a solvent that is adapted to the connecting layer. As a consequence, the connecting layer is detached. As a consequence, the sensor units detach from the connecting layer or the positioning substrate. The solvent in this case is selected so that the remaining components are not damaged.

A mechanical detaching characteristic (e.g., by a corresponding exertion of force, a normal stress, a bending stress, a shear stress, and/or a torsional stress) results in the connecting layer breaking or tearing off from the sensor units. The connecting layer in this case is configured so that the sensor units and the further components are also not damaged in the event of a rupturing or tearing force.

After positioning the sensor boards on the module carrier, the connecting layer and the positioning substrate may be detached from the sensor units. The positioning substrate is an aid for the positioning of the sensor units and not or is not necessarily a part of the finished detector module. Therefore, the positioning substrate may be removed after positioning the sensor units relative to the module carrier. For this purpose, one or multiple of the above-described detaching characteristics of the connecting layer may be used.

BRIEF DESCRIPTION OF THE DRAWINGS

The invention is once again further explained below with reference to the attached figures with the aid of embodiments. In this case, same components are provided with same reference characters in the different figures. Relative position information and/or direction information such as, for example, "on" relates, provided that nothing different is disclosed, to a direction perpendicular to the positioning substrate on the side having the connecting layer. In general, the figures are not to scale. In the drawings.

DETAILED DESCRIPTION

Figure 1:
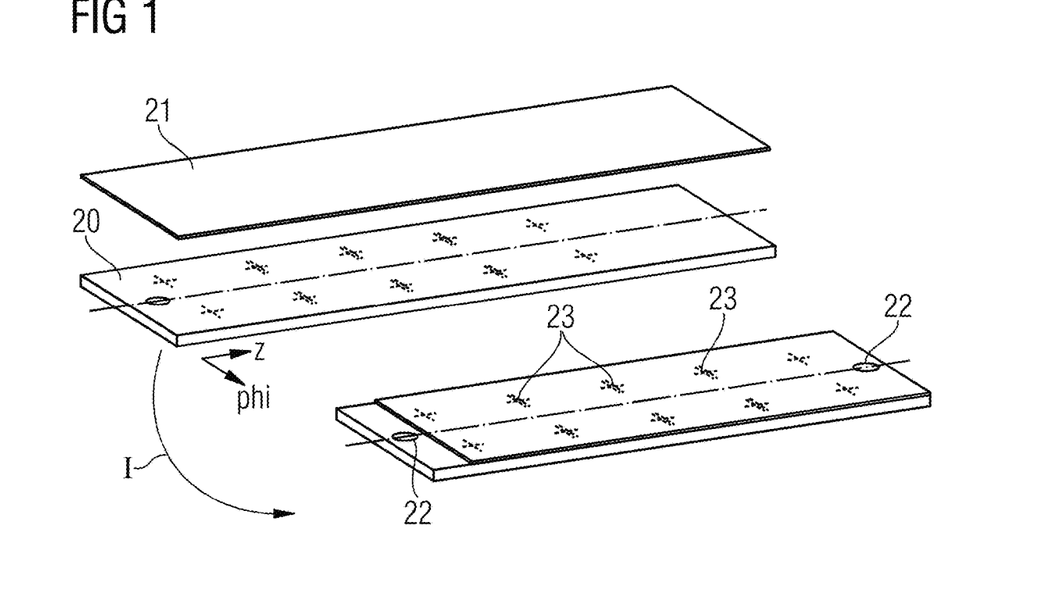
FIG. 1 shows a schematic perspective illustration of starting components and product of a method act I of an embodiment of a method for positioning sensor units.

FIG. 1 to FIG. 5 illustrate, in a schematic manner, in perspective views, method acts of a method in accordance with the present embodiments for positioning sensor units in a detector module of a CT device having the respective starting components and products of the method. In this case, FIG. 1 illustrates an act I of the method.

In act I, a positioning substrate 20 is provided. The positioning substrate 20 is, for example, essentially flat and is made of glass with a rectangular base. In this case, the positioning substrate 20 has a smooth surface having deviations of at most 5 μm. The positioning substrate extends with a longitudinal direction (e.g., illustrated by a central axis) in a direction z. The direction z corresponds in the case of the installation in a CT device to the direction of a craniocaudal axis of a patient on a patient couch in the CT device (not illustrated here). Further, a direction phi that is perpendicular to the direction z is illustrated, which corresponds in the case of the installation in a CT device to a circular circumferential direction around the craniocaudal axis of the patient. The direction phi corresponds to, for example, a transverse direction of the positioning substrate 20.

Perpendicular to the directions z and phi, the positioning substrate 20 has a thickness that is selected so that the positioning substrate 20 has sufficient mechanical characteristics for the positioning such as breaking strength, bending strength, and the like.

In the two end regions in its longitudinal direction, the positioning substrate 20 has a hole 22 with a defined radius in each case centrally in relation to its transverse direction. The hole 22 acts as a first mechanical positioning element 22.

Further, the positioning substrate 20 has optical markers 23 in the form of positioning crosses. The optical markers 23 are arranged in four groups of four. The optical markers 23 of a group of four are positioned in this case in each case in the corners of a rectangle, where the rectangles are arranged spaced equidistantly in the direction z and in the direction phi arranged centrally in the direction of the central axis of the positioning substrate 20. The spacing between adjacent rectangles in this case is in the magnitude of a pixel of the sensor units 24 (cf. FIG. 2) and, for example, smaller than a pixel.

A connecting layer 21 is now applied in act I to the positioning substrate 20. The positioning substrate 20 is made, for example, from a polymer film that, after a specific time, evaluates and in this manner temporarily connects the sensor units 24 that are to be positioned, in the next act II, to the positioning substrate 20. For the temporary embodiment of the connection, the connecting layer 21 has, for example, an optical detaching characteristic. In other words, after the connecting layer has cured, the connection to the sensor units 24 may detach again due to the effect of radiation in the UV spectrum in that the polymer compounds that occur during the curing are destroyed by the UV radiation.

Figure 2:
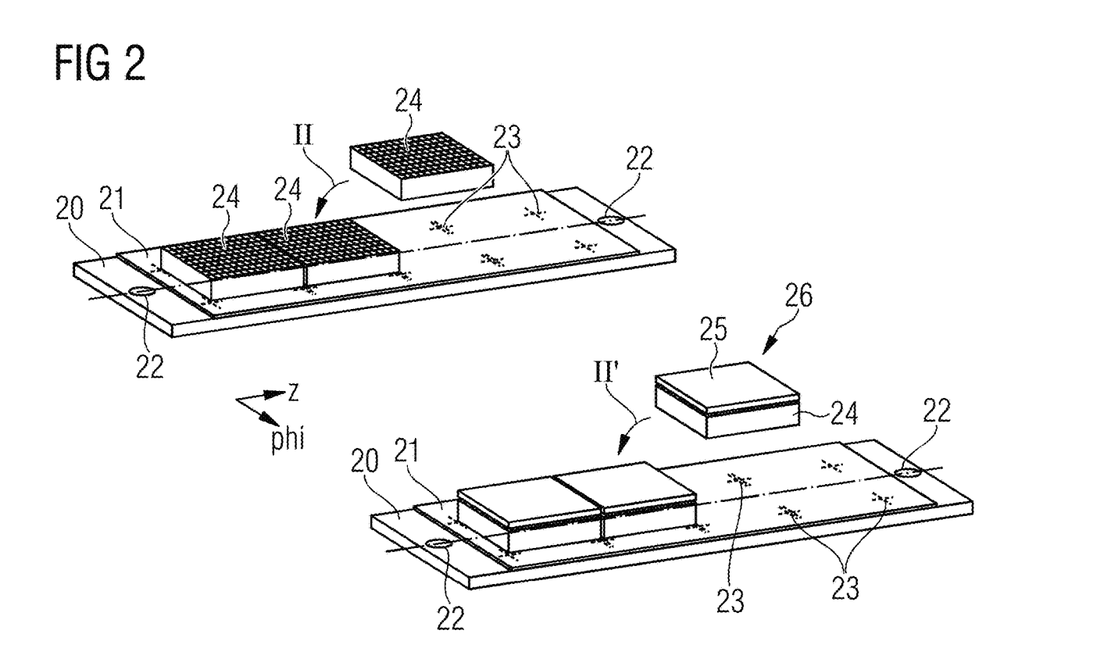
FIG. 2 shows an illustration as in FIG. 1, but for a method act II and an alternative method act II'.

FIG. 2 illustrates act II in which the sensor units 24 are positioned relative to the positioning substrate 20. The positioning takes place, for example, in an image processing-controlled manner. In this case, the position of the respective sensor unit 24 and the positions of the allocated groups of four optical markers 23 are acquired by at least one camera. The optical markers 23 indicate in this case the end position of the corners of the respective sensor unit 24. Due to an automatic alignment of the position of the optical markers 23 with the positions of the corners of the sensor unit 24, it is possible to control a positioning device, such as, for example, a robot arm, in a feedback loop so that the positioning device positions the sensor unit 24 as precisely as possible. The deviations or the tolerance in the image processing-controlled positioning may be, in this case, for example, smaller than 15 μm, smaller than 10 μm, or smaller than 5 μm. The individual pixels of a sensor unit 24 are, for example, in each case represented as a grid on the sensor unit 24.

After the positioning of all the sensor units 24, the connecting layer 21 cures in order to produce a temporary connection at a fixed position (e.g., being mechanically rigid) between the sensor units 24 and the positioning substrate 20.

FIG. 2 further illustrates an alternative act II'. Here, prefabricated sensor readout arrangements 26, which in each case include a sensor unit 24 and a readout unit 25, are positioned on the positioning substrate 20 in an image processing-controlled manner, as described above. The sensor readout arrangements 26 are prefabricated in that solder is introduced in a ball grid array (not illustrated here) between the two components, and the components are connected to one another according to a reflow soldering method in an electrically conductive and mechanically rigid manner. In this case, pixel by pixel electrically conductive contacts are formed between the readout unit 25 and the sensor unit 24 by the individual solder balls of the ball grid array. In embodiment variants, the sensor readout arrangements 26 may also include multiple readout units 25 per sensor unit 24.

After act II, the same product as according to act II' is obtained if after positioning the sensor units 24 on the positioning substrate 20 (e.g., and where necessary curing the connecting layer 21) as already described during act II' in each case at least one readout unit 25 is positioned on the sensor units 24 and connected by a ball grid array and reflow soldering. The positioning of the readout units 25 may take place in this case, as likewise already described, in an image processing-controlled manner and relative to the positioning substrate 20 or optical markers 23 of the positioning substrate 20. Sensor readout arrangements 26 are likewise produced in this manner from the sensor units 24 and the readout units 25.

Figure 3:
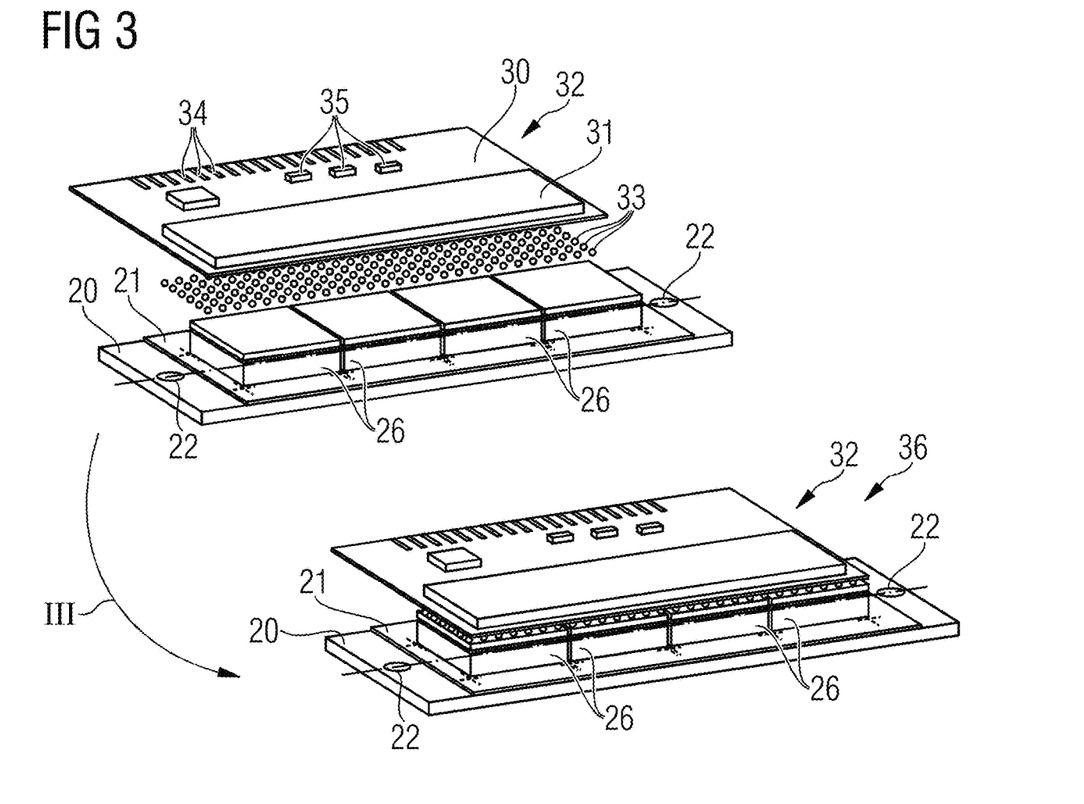
FIG. 3 shows an illustration as in FIG. 1, but for a method act III.

In FIG. 3, the four sensor readout units 26 that are arranged using the positioning substrate are connected to an electronics board 32. This likewise takes place using a ball grid array 33 and a reflow solder method as essentially already described. During the reflow soldering, a lower temperature and a solder that is suitable for the lower temperature may be worked with in order to not impair the electrical contacts within the sensor readout arrangements 26.

The electronics board 32 includes a flexible base layer 30 on which a stiffening element 31 is arranged in a region in which the sensor readout arrangements 26 are to be contacted. This is used for the additional mechanical stabilization. The electronics board 32 further has a number of electronic components 35 with which the measuring data that is acquired by the sensor units 24 and that is readout by the readout units 25 are further processed and relayed. For the relaying, the electronics board 32 has electrical contacts 34 that are connected to other components of the detector or the CT device in order to finally achieve a reconstruction of a CT image from the measurement data.

The connection or combination that is obtained in this manner of the sensor readout arrangements 26 and the electronics board 32 is referred to as a sensor board 36.

Figure 4:
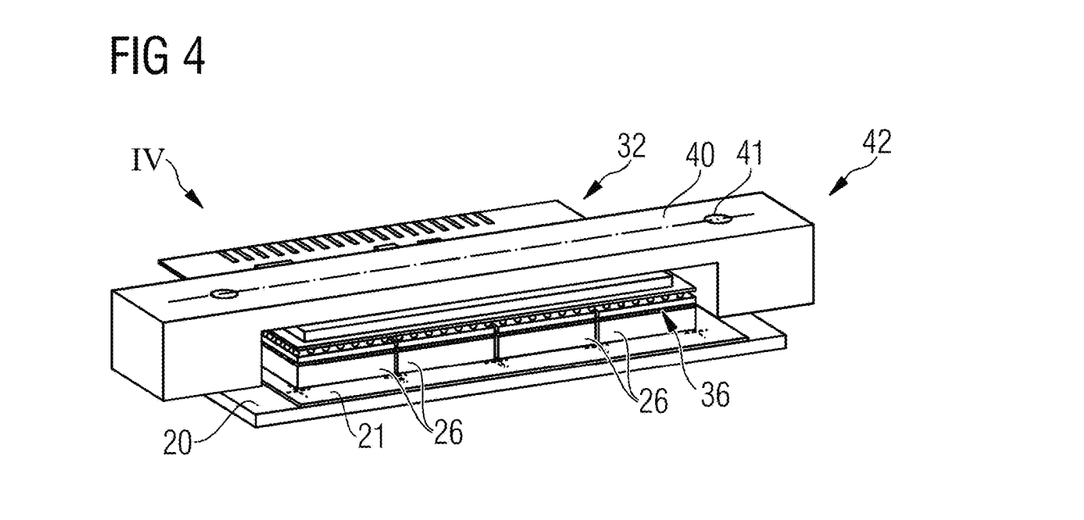
FIG. 4 shows an illustration as in FIG. 1, but for a method act IV.

FIG. 4 illustrates method act IV in which the sensor board 36 is positioned by the positioning substrate 20 relative to a module carrier 40. For this purpose, positioning pins or dowel pins are inserted through the holes 22 in the positioning substrate 20 or through the first mechanical positioning elements 22 (see FIG. 1 to FIG. 3) and through corresponding holes 41 in the module carrier 40 or through the second mechanical positioning elements 41. By manufacturing the corresponding positioning elements 22, 40 and the positioning pin as precisely as possible with low tolerances (e.g., as self-centering), overall, it is possible to achieve a positioning precision of the sensor units 24 relative to the module carrier 40 of, for example, below 10 µm or below 5 µm. This represents a clear improvement with respect to the manufacturing method that is known from practical experience.

The sensor board 36 is attached to the module carrier 40 and connected or joined together with the module carrier in a mechanically rigid manner. This may take place, for example, using mechanical positive-fit and/or non-positive-fit connection. Alternatively or in addition thereto, the sensor board 36 may be adhesively bonded to the module carrier 40 using a suitable material. The connection or combination of the sensor board 36 and the module carrier 40 is referred to as a detector module 42. The detector module 42 may, however, also include further components as is further described below.

Figure 5:
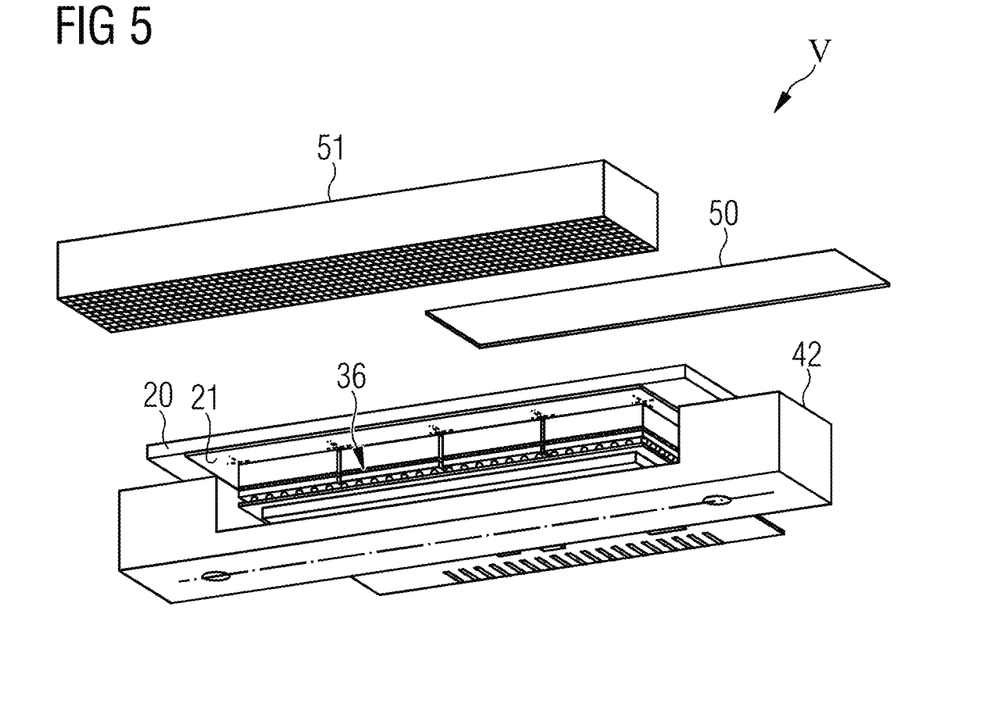
FIG. 5 shows an illustration as in FIG. 1, but for a method act V.

FIG. 5 illustrates act V in which the positioning substrate 20 and the connecting layer 21 are detached from the sensor units. After the sensor board 36 is connected to the module carrier 40 in a fixed manner, initially the positioning pins are removed from the mechanical positioning elements 22, 41. Subsequently, the connecting layer 21 is irradiated with UV light according to its optical detaching characteristic until the connecting layer detaches from the sensor units.

After removal from the positioning substrate 20 and the connecting layer 21, it is possible to attach further components of the detector module 42 to the now free side of the sensor units 26. In an exemplary manner, an HV film 50, for example, is illustrated that is brought into electrical contact with the sensor units 26. The HV film supplies the sensor units 26 during operation with a suitable prestressing. Further, an anti scatter grid 51 (ASG) is arranged on the HF film in order to shield the sensor units 26 from oblique incident radiation during operation.

Using the described embodiment of the method in accordance with the present embodiments, a detector module 42 that has a high degree of positioning precision of the sensor units 26 in relation to the module carrier 40 is consequently obtained. Due to mechanically precise manufacturing of the mechanical connecting elements 22, 41 and the precise positioning of the first mechanical connecting elements 22 with respect to the second mechanical connecting elements 41, it is also possible altogether to achieve a high degree of positioning precision of the sensor units 26 in relation to the detector.

Since, as already described in the introduction, the image quality that may be achieved using a CT device at ever greater resolution (e.g., ever smaller pixels) depends on a precise positioning of the pixels or of the sensor units that include the pixels, the present embodiments consequently overall also contribute to an improvement of the image quality (e.g., of photo-counting direct-conversion CT devices) and simplifies their manufacturing process.

Reference is again made to the fact that the apparatuses and method that are described above in detail are only embodiments that may be modified in various ways by the person skilled in the art without departing the scope of the invention. Further, the use of the indefinite article "a" or "an" does not rule out that the relevant features may also be provided multiple times. Likewise, the terms "device", "unit", "board", "arrangement" or "module" do not rule out that these are made of multiple components that, if not otherwise described, where necessary may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for positioning sensor units in a detector module for a computed tomography (CT) device, the method comprising:
    arranging a connecting layer on a positioning substrate;
    positioning a number of sensor units and a number of readout units, forming sensor readout arrangements, relative to the positioning substrate, wherein the number of sensor units are temporarily connected to the positioning substrate at a fixed position by the connecting layer;
    positioning a number of electronics boards and producing conductive connections between the number of electronics boards and contacts of the number of readout units, such that a number of sensor boards are obtained; and
    positioning the number of sensor units and positioning the number of sensor boards by the positioning substrate relative to a module carrier and attaching the number of sensor units to the module carrier, such that a detector module is obtained,
    wherein the positioning substrate has optical markers, and the positioning of the number of sensor units and the number of readout units relative to the positioning substrate takes place in an image processing-controlled manner.

2. The method of claim 1, wherein the positioning substrate has first mechanical positioning elements for positioning on second mechanical positioning elements of the module carrier.

3. The method of claim 1, wherein positioning the number of sensor units and the number of readout units comprises:
    positioning relative to the positioning substrate and temporarily connecting at least one sensor unit of the number of sensor units on the positioning substrate at a fixed position by the connecting layer.

4. The method of claim 1, wherein the positioning substrate is made of silicon, steel, or glass.

5. The method of claim 1, wherein the connecting layer has a thermal, an optical, a chemical, and/or a mechanical detaching characteristic.

6. The method of claim 1, wherein the positioning substrate is transparent for optical radiation.

7. The method of claim 1, further comprising detaching the connecting layer and the positioning substrate from the number of sensor units.

8. The method of claim 1, wherein the positioning of the number of sensor boards relative to the module carrier takes place in an image processing-controlled manner.

9. The method of claim 1, wherein positioning the number of sensor units and the number of readout units comprises:
   positioning relative to the positioning substrate and conductively connecting in each case at least one readout unit of the number of readout units on the number of sensor units, which are respectively connected to the positioning substrate, such that a number of sensor readout arrangements are obtained.

10. The method of claim 1, wherein positioning of the number of sensor units and the number of readout units comprises:
    positioning relative to one another and conductively connecting at least one readout unit of the number of readout units on a respective sensor unit of the number of sensor units, such that a number of sensor readout arrangements are obtained; and
    positioning the number of sensor readout arrangements relative to the positioning substrate,
    wherein the number of sensor units of the number of sensor readout arrangements are temporarily connected to the positioning substrate at a fixed position by the connecting layer.

11. The method of claim 1, wherein the number of electronics boards are configured as flexible electronics boards, rigid flexible electronics boards, fixed-flexible-fixed electronics boards, or fixed electronics boards.

12. The method of claim 1, wherein detaching the connecting layer and the positioning substrate from the number of sensor units comprises detaching the connecting layer and the positioning substrate from the number of sensor units after positioning the number of sensor boards on the module carrier.

13. The method of claim 1, wherein the positioning of the number of sensor units and the number of readout units relative to the positioning substrate takes place in an image processing-controlled manner using the optical markers.

14. A detector module for a computed tomography (CT) device, the detector module comprising:
   a connecting layer arranged on a positioning substrate;
   a number of sensor units and a number of readout units, forming sensor readout arrangements, positioned relative to the positioning substrate, wherein the number of sensor units are temporarily connected to the positioning substrate at a fixed position by the connecting layer; and
   a number of electronics boards and conductive connections between the number of electronics boards and contacts of the number of readout units, such that a number of sensor boards are obtained,
   wherein the number of sensor units and the number of sensor boards are positioned by the positioning substrate relative to a module carrier, and the number of sensor units are attached to the module carrier, such that a detector module is obtained, and
   wherein the positioning substrate has optical markers, and the number of sensor units and the number of readout units are positioned relative to the positioning substrate in an image processing-controlled manner.

15. A use of a positioning substrate so as to position sensor units relative to a module carrier of a detector module of a computed tomography (CT) device, wherein:
   a number of sensor units and a number of readout units, forming sensor readout arrangements, are positioned relative to the positioning substrate, the number of sensor units being temporarily connected to the positioning substrate at a fixed position by a connecting layer;
   a number of electronics boards are positioned, and conductive connections between the number of electronics boards and contacts of the number of readout units are produced, such that a number of sensor boards are obtained; and
   the number of sensor units and the number of sensor boards are then positioned by the positioning substrate relative to the module carrier and are attached to the module carrier, such that the detector module is obtained,
   wherein the positioning substrate has optical markers, and the positioning of the number of sensor units and the number of readout units relative to the positioning substrate takes place in an image processing-controlled manner.

* * * * *